(12) United States Patent
Yamada

(10) Patent No.: US 6,475,513 B1
(45) Date of Patent: Nov. 5, 2002

(54) SKIN-CARE POUCH

(76) Inventor: Kiyoshi Yamada, 1-2-25, Kishidadonishi, Higashiosaka-shi, Osaka (JP)

( * ) Notice: Subject to any disclaimer, the term of this patent is extended or adjusted under 35 U.S.C. 154(b) by 0 days.

(21) Appl. No.: 09/963,407

(22) Filed: Sep. 27, 2001

(30) Foreign Application Priority Data

Apr. 9, 2001 (JP) ........................................ 2001-109958
May 17, 2001 (JP) ........................................ 2001-147651

(51) Int. Cl.⁷ .................................................. A61K 9/70
(52) U.S. Cl. ........................ 424/443; 424/400; 424/401; 424/486; 424/125; 424/699; 424/700; 424/701; 424/715; 424/725; 424/750; 428/34.3; 428/34.5; 428/35.7
(58) Field of Search ................................ 424/400, 401, 424/443, 486, 125, 699, 700, 701, 715, 725, 750; 428/34.3, 35.7, 34.5

(56) References Cited

U.S. PATENT DOCUMENTS 6,187,324 B1 * 2/2001 Ogi et al.

FOREIGN PATENT DOCUMENTS

| JP | 11267150 A | * 10/1999 |
| JP | 2001-106216 | * 10/2000 |

* cited by examiner

*Primary Examiner*—Leon B. Lankford, Jr.
*Assistant Examiner*—Ruth Davis

(57) ABSTRACT

A skin-care pouch includes a sealed enclosure storing therein a number of carbide aggregations including carbides in the form of small pieces, granules or particles, water-absorbent shape-keeping agent which is gelled by absorbing water upon contact therewith and so on. The sealed enclosure in the form of a bag is formed of a fabric capable of permeating water and the carbides therethrough to be placed into contact with a desired portion of skin where care or treatment thereof is desired.

10 Claims, 9 Drawing Sheets

SKIN-CARE POUCH

BACKGROUND OF THE INVENTION

1. Field of the Ivention

The present invention relates to a skin-care pouch which is supplied, for use, with water for applying a skin-care substance such as find powder of carbides or wood vinegar contained therein to the skin as the substance is oozed through a sealed pouch enclosure formed of a porous fabric.

2. Description of the Related Art

Generally, women have been highly concern about their cosmetic skin care for the face, hands, etc. A great variety of skin-care products have long been on the market to meet the demand.

In recent years, there has been a more universal growing concern about skin care regardless of sex or generations for the skin-health purpose in general such as treatment or relief of skin troubles such as pimps, hay fever, and atopic dermatitis. Met with this new market demand, the industries have introduced a variety of skin-care products.

Referring to face skin care products for example, these products are generally available in the form of skin lotion when they are designed for keeping skin moisture or in the form of milky lotion or cream when designed for supplementing oil to the face skin from which oil has been removed by washing with soap or water.

However, such conventional skin-care products have the problems of incompatibility to some users' skin and difficulty experienced by the user in the case of milky or cream when determining and applying a proper portion of the substance.

In view of the above, there remains a need for a skin care product which can overcome or at least reduce the above-described drawbacks of the prior art.

Under these circumstances described above, a discovery was made that when fine powder of carbides comprised mainly of "Bincho" charcoal or the like is dipped in water and then applied directly to the skin, effective components of the carbides will elute to provide its sterilizing, moisture supplementing or oil removing effect to the skin and also that such components of the carbide are mild to the skin, not causing skin problems. The "Bincho" charcoal is a type of high-quality charcoal made from holm oak (*Quercus phillyraeoides*), a specialty product of a region called "Kumano" in Japan.

Based on the above finding, the present inventor first conceived of a product in the form of a pouch made of a mesh-like or porous fabric storing therein fine powder of Bincho charcoal therein and actually made a trial product.

When this trial product was put to use, however, water and a portion of the fine powder carbide were just lost before they could be used as they escaped through the pouch fabric. So that, when the pouch was about to applied to the skin, the fine powder of carbide hardly oozed out of the pouch. Hence, it was not possible to apply a sufficient amount of the substance to the skin. Moreover, the other portion of the fine powder remaining within the pouch had lost fluidity with water absorption therein so that the entire pouch became like a hard block, uncomfortable to be applied to the skin. Therefore, the product was proved unsuitable for commercial production unless some improvement was made thereon.

On the other hand, wood vinegar is known. This wood vinegar liquid is produced by diluting or refining liquid concentrate obtained by cooling and condensing smoke generated from a charcoal kiln during production of charcoal. The conventional applications of the wood vinegar liquid include their uses as soil activating agent or insecticide dusting agent to be contained in agricultural or horticultural products. Wood vinegar is also used as a skin relief agent for direct application for relief of atopic dermatitis or athlete's foot or it is sometimes provided in the form of a bathing product to be put into a bathtub for the same purpose. These applications are possible because the wood vinegar liquid is comprised of natural components. There are may other applications of wood vinegar liquid, not described here.

Especially, the component analysis has revealed that wood vinegar liquid contains various minerals and ionic substances such as calcium ion, magnesium ion, etc. And, it has been confirmed that these components are beneficial for skin care. For example, according to a report published by a certain cosmetics research institute, calcium ion and magnesium ion are found in abundance between the epidermis and stratum corneum, indicating that supplement of calcium ion and magnesium ion will be effective for conditioning skin texture and maintaining healthy skin. From these findings, it is understood that wood vinegar is useful for skin care.

In recent years, as described hereinbefore, there is a growing concern about skin care not only among females in limited generations, but among general population regardless of sex or ages.

Under such circumstances, however, the industries' have not yet fully exploited the possibility of using wood vinegar liquid as a skin care agent. And, those wood vinegar products currently on the market are mainly in the form of a bottled product.

However, when a user uses such bottled wood vinegar liquid product as skin care agent, as the wood vinegar per se is liquid, the user will usually soak absorbent gauze or cotton ball or the like in the liquid and apply this to his/her skin or will prefer to use a towel dedicated for this use because of a characteristic smell of the wood vinegar liquid and soak it in the liquid and apply it to the skin.

Therefore, in order to use wood vinegar liquid as a skin care agent, the user needs to prepare separately such an article as absorbent gauze and needs also to clear it away after use. Moreover, as wood vinegar has a strong characteristic smell, the user will have to handle it with great care so that the liquid will not be attached to the clothes. For these reasons, the bottled wood vinegar liquid, as a skin care agent, is an unhandy product and also presents the difficulty of its use by an appropriate portion. Faced these difficulties and inconvenience, many users tend to just give up using wood vinegar liquid as skin care agent before long although they desire to use it regularly for an extended period of time.

SUMMARY OF THE INVENTION

The present invention has been made in view of the above-described state of the art. A first object of the invention is to provide a skin-care pouch containing fine powder of carbide which oozes out of a sealed enclosure of the pouch when needed for its application to the skin, the pouch also giving comfortable feel to the skin when contacted therewith.

A second object of the invention is to provide such pouch as a handy and convenient product.

For accomplishing the first object noted above, according to one aspect of the present invention, there is proposed a skin-care pouch comprising: a number of carbide aggregations including carbides in the form of small pieces, granules or particles; water-absorbent shape-keeping agent which is gelled by absorbing water upon contact therewith; and a sealed enclosure storing the carbide aggregations and the water-absorbent shape-keeping agent therein, the sealed enclosure being formed of a fabric capable of permeating water and the carbides therethrough.

With the above-described skin-care pouch according to the invention, when the pouch is soaked in warm or cold water and rubbed or squeezed therein, the water enters the sealed enclosure to gel the water-absorbent shape-keeping agent therein, so that the pouch keeps its shape. When withdrawn out of the water, the pouch is maintained under the moist condition by retaining the water absorbed therein. Then, when placed in contact with skin under this condition, the pouch allows the fine powder of carbides to ooze out in a controlled manner together with the water to be applied to the skin. As a result, a sufficient amount of carbides may be applied to the skin.

Further, as the inner content of the water-soaked pouch is maintained in shape under the gelled condition by the water-absorbent shape-keeping agent, the content retains high fluidity, providing good cushioning effect to improve the skin feel of the pouch during application.

Accordingly, as the pouch is capable of oozing i.e. dispensing the fine powder carbide therein gradually therethrough, the pouch may be used for repeated times and for a long period of time. In these ways, the skin-pouch achieves high quality in use as well as high reliability as well.

In the above, the fine powder carbides which can pass the fabric of the sealed enclosure are caused to be contained in abundance within the carbide aggregations from the beginning. For use, the find powder of carbide is gradually generated from the carbide aggregations by e.g. rubbing or squeezing and kneading the pouch containing the aggregations.

Preferably, in the skin-care pouch having the above-described construction the carbide aggregations comprise hard charcoal.

The term "hard charcoal" refers to a kind of charcoal having high density and hardness. The hard charcoal is manufactured by baking raw material of oak, chestnut or the like in a stone kiln at a high temperature ranging generally between 900° C. and 1,400° C., removing the baked product out of the kiln and quenching it by putting a mixture, called quenching powder, of earth, coal and carbon dust over it, so that the finished hard charcoal has an ash gray surface. It is said that of various types of hard charcoals, the Bincho charcoal made by baking holm oak is the best in quality.

The hard charcoal, especially Bincho charcoal, has high hardness, thus less possibility of smearing the skin black with its fine powder than other charcoals. Therefore, the skin-care pouch using hard charcoal can achieve even better quality in use. Moreover, in the case of hard charcoal, especially Bincho charcoal, when particles or granules thereof are rubbed against each other within the pouch, they will not be crushed too easily to produce an excessive amount of powder at one time. In addition, once pulverized, the resultant particles are very fine, so that these particles oozing out of the sealed enclosure provide smooth and comfortable i.e. non-irritating feel to the skin. Therefore, even those users having a sensitive or weak skin can use the pouch without much worrying.

Alternatively, in the skin-care pouch of the invention, the carbide aggregations may comprise bamboo charcoal.

As its name indicates, bamboo charcoal is made from bamboo tree by baking it to carbonize its bamboo fibers. The bamboo charcoal has fine texture and high hardness. Therefore, like the hard charcoal described above, it provides less possibility of smearing the skin black with its fine powder. The bamboo charcoal provides another advantage of easier processing because of its thinness. Then, it becomes readily possible to obtain the carbide aggregations including carbides in the form of small pieces, granules or particles in the optimum conditions.

Preferably, in the skin-care pouch having the above-described construction, the carbide aggregations further include activated carbon.

Namely, if the carbide aggregations contain activated carbon having a different hardness from the other carbides, when the other carbides are rubbed against the activated carbon having a higher or lower hardness, the amount of carbide fine powder produced will increase, compared with a case when carbides of a same hardness are rubbed against each other. Therefore, it becomes possible to increase the amount of carbide fine powder to ooze out of the sealed enclosure.

Consequently, it becomes possible to optimize the oozing amount of carbides by appropriately setting the ratio of the activated carbon to be mixed in the aggregations.

Furthermore, the activated carbon provides an economic advantage since it is cheaper than the other carbides or charcoals. Therefore, when compared with a case when the carbide aggregations consist of a single kind of carbide, the aggregations mixed with activated carbon provide the possibility of producing lower-priced products.

Still preferably, in the skin-care pouch having the above-described construction, the water-absorbent shape-keeping agent comprises a number of water-absorbent polymers in the form of granules or powder.

That is, the water-absorbent polymers will absorb water and expand when water is supplied into the sealed enclosure. In the course of this, the polymer particles or granules will not adhere to each other. Therefore, in the expanded condition of the sealed enclosure too, the pouch can effectively maintain the fluidity of its inner content. Therefore, by rubbing or squeezing the sealed enclosure, the carbides of the carbide aggregations present between the expanded water-absorbent high polymer particles or granules may be sufficiently rubbed against each other, thereby to promote the production of the carbide fine particles to be oozed out together with the water present therebetween.

As a result, after repeated uses or use for an extended period of time, the oozing amount of the carbide fine powder can still be maintained to be substantially same as the oozing amount at the beginning of the use of the pouch.

Still preferably, in the skin-care pouch having the above-described construction, the water-absorbent shape-keeping agent comprises gelling agent.

When water is supplied into the pouch, the gelling agent becomes gel having high fluidity. So, when the inner content of the sealed enclosure is expanded, the content can retain the fluidity. Accordingly, by rubbing or squeezing the pouch, the water-absorbent shape-keeping agent in the form of gel will be displaced around therein to ooze the carbide fine powder out of the sealed enclosure. And, after repeated uses or use for an extended period of time, the oozing amount of the carbide fine powder can still be maintained to be substantially same as the oozing amount at the beginning of the use of the pouch.

In this case, by increasing the amount of carbide particles or granules relative to the amount of gelling agent, the oozing amount of the carbide fine powder may be increased as desired.

Preferably, the sealed enclosure further stores therein chips impregnated with aromatic substance.

For example, by impregnating chips of e.g. oak with an aromatic substance such as oak oil or herb oil and then storing them inside the sealed enclosure, aroma will be generated from the sealed enclosure during use of the pouch. Hence, the pouch can provide an aromatherapy effect. Moreover, after application to the skin, the aroma of the aromatic substance will be left on the skin, so that the negative impression of the pouch due to the black-colored carbides oozing out of the sealed enclosure may be offset by the aroma and can even be changed into a positive and pleasant impression.

Still preferably, in the skin-care pouch having the above-described construction, the sealed enclosure further stores therein natural medication containing skin moisture keeping component.

For instance, when such natural medication in the form of chips or strips are stored within the sealed enclosure, when water is supplied through into the sealed enclosure, the moisture-keeping component will be dissolved out of the natural medication and then ooze out through the sealed enclosure. Further, when the pouch is rubbed or squeezed, the natural medication will be rubbed by the carbide aggregations also stored in the sealed enclosure, so that elution of the component of the natural medication will be promoted and its elution amount will decrease gradually. However, with repeated uses of the pouch, the moisture-keeping component can still be oozed out.

For accomplishing the second object described hereinbefore, according to a second aspect of the present invention, there is proposed a skin-care pouch comprising wood vinegar in the form of powder and a sealed enclosure storing the wood vinegar powder therein, the sealed enclosure being formed of a texture capable of permeating water therethrough.

With the skin-care pouch having the above construction, when the pouch is soaked in warm or cold water to supply water into the sealed enclosure, the wood vinegar powder stored within the sealed enclosure will be dissolved in the water and this water solution will ooze out of the sealed enclosure to come into direct contact with the skin for its care. Therefore, compared with the conventional bottled wood vinegar product needing preparation of gauze or towel dedicated for use therewith, the skin-care pouch of the invention allows ready use of wood vinegar.

Moreover, with this skin-care pouch, wood vinegar powder is liquefied upon supply of water into the sealed enclosure. Then, the pouch under its ordinary, non-use condition is light-weight and handy, allowing easy storage and transportation. Further, since the product may be put on the market in the form of a package including a plurality of such pouches, the transportation and handling are easy in any stage of distribution, storage, display and personal storage by a user. Also, since water is supplied only immediately before use, corrosion or quality deterioration of the product can be restricted, thus reducing necessity of corrosion inhibitor advantageously.

Further, the application of this skin-care pouch is not limited to direct application of wood vinegar to the skin like the conventional product. The entire pouch may be put into a bath tub, wash basin, watering can, etc. to be submerged in water therein for dissolving the wood vinegar powder in the water. As a still further alternative, the pouch may be put into a shoe under dry condition without supply of water to the pouch.

The wood vinegar powder can be processed from natural wood vinegar liquid by any appropriate conventional method such as high-speed freeze-drying method, vacuum drying method, etc.

For accomplishing the second object noted above, the invention further proposes a skin-care pouch comprising a number of gel aggregations in the form of small pieces or granules impregnated with wood vinegar; and a sealed enclosure storing therein the gel aggregations, the sealed enclosure being formed of a fabric capable of permeating water therethrough.

With the skin-care pouch having the above-described construction, by supplying water into the sealed enclosure, wood vinegar will be dissolved out of the gel aggregations stored in the sealed enclosure and can be oozed out of the sealed enclosure as a water solution. Then, by rubbing this pouch oozing the wood vinegar against the skin, the skin can be treated. Therefore, compared with the conventional bottled wood vinegar product needing separate preparation of gauze or towel dedicated for use therewith, the skin-care pouch of the invention allows ready use of wood vinegar liquid.

Moreover, with this skin-care pouch of the above construction, the wood vinegar impregnated in the gel aggregations will elute gradually upon supply of and subsequent contact with water. So that, the pouch may be used repeatedly until all of the gel aggregations are eluted with water supply.

In the above, the gel aggregations comprise gels of e.g. gelatinizer impregnated with wood vinegar and formed into the shape of small pieces or granules.

Also, what is referred to as "wood vinegar" in this invention represents wood vinegar made by diluting or refining liquid concentrate obtained by cooling and condensing smoke generated during manufacture of soft charcoal made with a low combustion temperature of a charcoal kiln or hard charcoal made with a high combustion temperature of the same or represents also bamboo vinegar made from bamboo tree.

Preferably, in the skin-care pouch having the above-described construction, the sealed enclosure further stores therein a water-absorbent cushioning material.

Namely, as the water-absorbent cushioning material becomes expanded upon contact with water, this expanded material provides the pouch with a cushioning effect, thereby to improve the pouch's feel to the skin when the pouch is placed into contact therewith for treatment.

Further, by storing the water-absorbent cushioning material in the sealed enclosure together with the number of gel aggregations impregnated with wood vinegar, when the pouch is rubbed or squeezed for repeated use, the presence of the cushioning material can promote the elution of the wood vinegar from the gel aggregations, thus improving oozing condition thereof.

Still preferably, in the skin-care pouch having the above-described construction, the water-absorbent cushioning material comprises cotton.

That is, the cotton naturally has high water-absorptivity. Thus, by appropriately adjusting the squeezing amount of cotton before dipping it in water, the amount of water to be supplied can be readily controlled. That is, if the pouch is squeezed mildly and dipped in water under this condition, the amount of wood vinegar solution will be increased. Conversely, if it is squeezed tightly and dipped in water, the oozing amount of the solution will be less. In this way, the oozing amount can be adjusted as desired through adjustment of the squeezing degree of the pouch.

In the skin-care pouch having the above-described construction, the water-absorbent cushioning material may comprise a water-absorbent shape-keeping material which is gelled by absorbing water.

Namely, the gelling agent absorbs water to become highly fluid gel and the sealed enclosure swells up. Hence, during application, there occurs displacement of the gelled water-absorbent shape-keeping material within the sealed enclosure, so that the skin feel of the pouch is improved. Further, as a sufficient amount of water can be supplied into the sealed enclosure in association with the gelatinization of the gelling agent, it is possible to extend the usable time period of the pouch with a single supplement of water thereto.

In the skin-care pouch having the above-described construction, the water-absorbent cushioning material may comprise a number of water-absorbent polymers in the form of granules or powder.

That is, the water-absorbent polymers will absorb water and expand when water is supplied into the sealed enclosure. In the course of this, the polymer particles or granules will not adhere to each other. Therefore, in the expanded condition of the sealed enclosure too, the pouch can effectively maintain the fluidity of its inner content. Therefore, by rubbing or squeezing the sealed enclosure, the pouch can be rubbed or squeezed sufficiently to improve its skin feel. Further, as water can be supplied to the gaps between the expanded water-absorbent polymers, a sufficient amount of water can be supplied into the sealed enclosure through the gelatinization of the gelling agent, so that it is possible to extend the usable time period of the pouch with a single supplement of water thereto.

In the skin-care pouch having the above-described construction, the sealed enclosure may further accommodate therein a number of carbide aggregations including carbides in the form of small pieces, granules or particles.

That is, upon supply of water, the number of water-absorbent polymers acting as water-absorbent cushioning material are expanded. And, by rubbing or squeezing the sealed enclosure under this condition, the carbides, which are said to be useful for removal of oily substance from the skin, are rubbed against each other and pulverized into powder, so that this powder and the wood vinegar are together gradually oozed out of the sealed enclosure. In this manner, this skin-care pouch allows application of wood vinegar and carbides to the skin at one time.

Moreover, the inner content of the sealed enclosure supplied with water has high fluidity and cushioning property due to the water-absorbent cushioning material present therein. So that, the pouch's skin feel may be improved.

Still preferably, in the skin-pouch comprising carbides and/or wood vinegar, the sealed enclosure is formed of non-woven fabric made mainly of a synthetic resin which can be sealed by heat.

For instance, the content may be placed between two sheets of non-woven fabric and then opposing peripheral edges of these fabric sheets will be heat-sealed together to form a sealed enclosure. Alternatively, a single sheet of non-woven fabric may be folded into two equal portions, between which the content is placed. Then, the opposing peripheral edges of the folded portions are heat-sealed to form a sealed enclosure. In these ways, the skin-care pouch may be produced in an efficient manner.

Still preferably, in the skin-care pouch having the above-described construction, the sealed enclosure further stores therein tourmaline ores in the form of granules.

That is, in case the water supplied is warm water, the tourmaline can delay the skin's feeling cold at least to some extent. Tourmaline can provide also a negative-ion effect beneficial to the skin.

Further and other features and advantages of the invention will become apparent upon reading the following detailed description of its preferred embodiments with reference to the accompanying drawings.

DESCRIPTION OF THE PREFERRED EMBODIMENTS

[First Embodiment]

Figure 1:
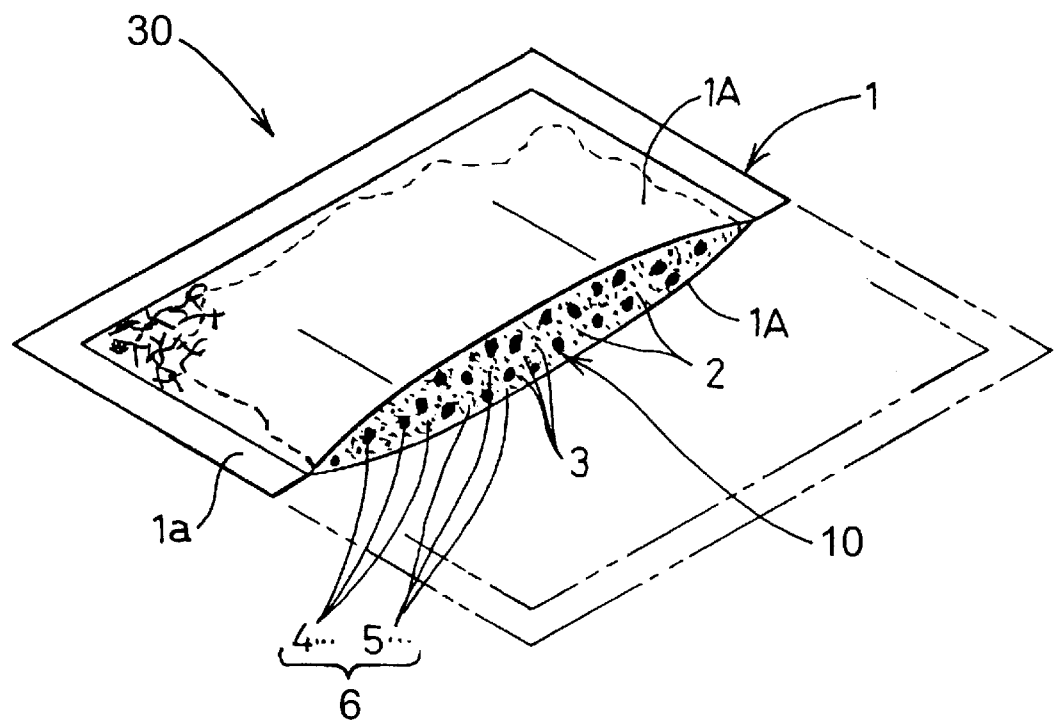
FIG. 1 is a perspective view showing a skin-care pouch according to a first embodiment of the invention in a condition when no water is supplied yet thereto.
Figure 2:
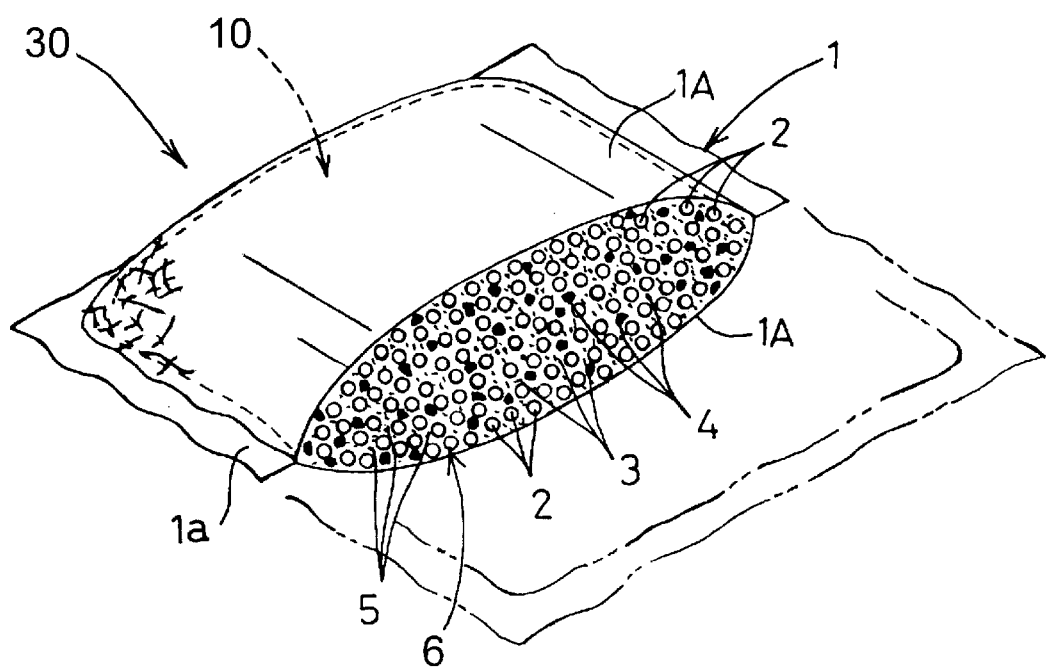
FIG. 2 is a perspective view showing the skin-care pouch according to the first embodiment in a condition when water has been supplied thereto.

As a first embodiment of the invention, construction of a skin-care pouch 30 will be described with reference to FIGS. 1–6.

This skin-care pouch 30 includes a sealed enclosure 1 which stores therein a mixed content 10 including a number of carbide aggregations 6 in the form of small pieces or granules, a number of water-absorbent polymers 2 . . . in the form of granules or powder acting as a water-absorbent shape-keeping agent which is gelled by absorbing water, and a number of tourmaline ores 3 . . . in the form of granules.

Figure 3:
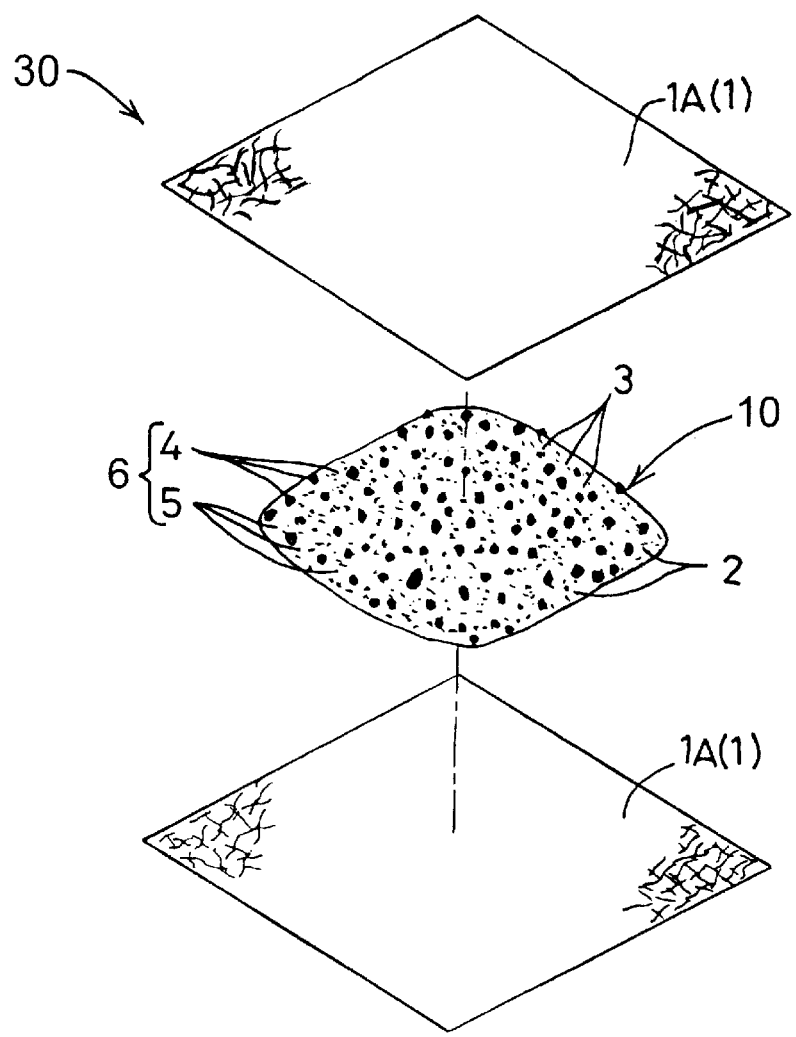
FIG. 3 is an exploded perspective view of the skin-care pouch according to the first embodiment.
Figure 4:
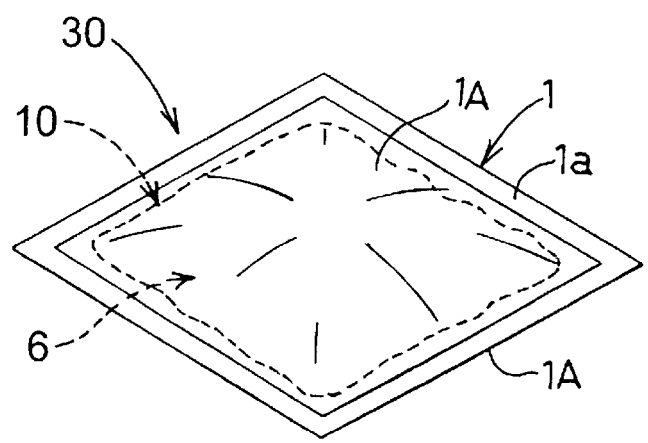
FIG. 4 is a perspective view showing the skin-care pouch according to the first embodiment in its finished condition as a commercial product.
Figure 5:
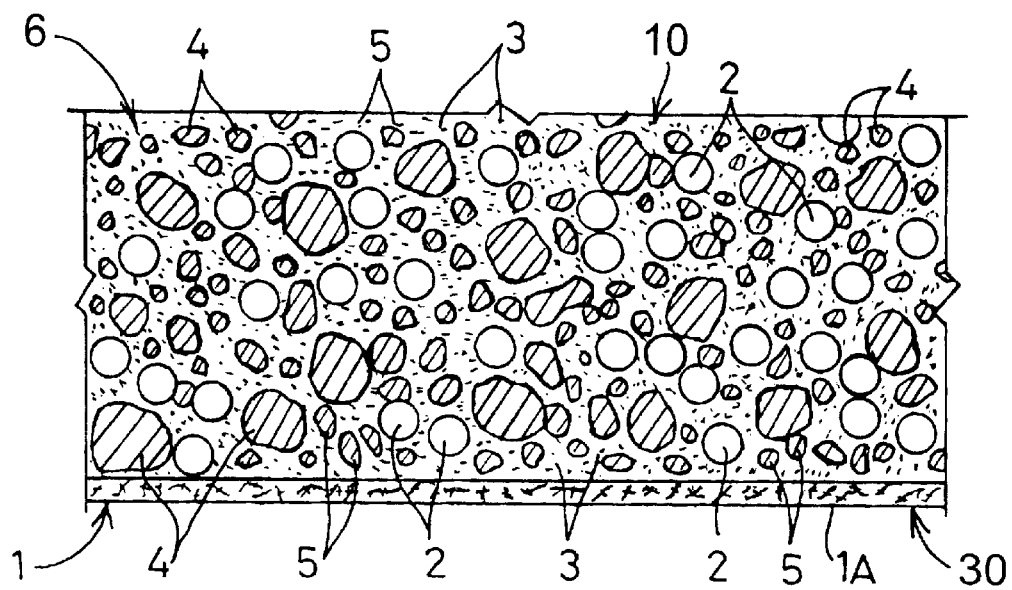
FIG. 5 is a section view showing principal portions, in an enlarged scale, of the skin-care pouch under the condition shown in FIG. 1.

The sealed enclosure 1 is made of a porous fabric capable of permeating water and the carbides 4 . . . , 5 . . . in the form of fine powder therethrough. The fabric comprises non-woven fabric sheets 1A, 1B made mainly of synthetic resin. Specifically, as shown in FIG. 3, between opposing faces of the two square-shaped non-woven fabric sheets 1A 1B with 10 cm side each, the mixture content 10 is placed and then joining margins 1a of about 5 mm in the peripheral edges of the opposed non-woven fabric sheets 1A, 1B are heat-sealed together, thereby to form the sealed bag or enclosure 1 as shown in FIG. 4.

The carbide aggregates 6 comprise mixture of a number of Bincho charcoals 4 . . . in the form of small pieces, granules, powder or fine powder and a number of activated carbons 5 . . . also in the form of small pieces, granules, powder or fine powder. In this particular embodiment, about 15 g of carbide aggregates are stored within the sealed enclosure 1, consisting of about 11 g of granules or powder of Bincho charcoals 4 . . . and about 4 g of granules or powder of activated carbons 5 . . .

The granule or powder Bincho charcoals 4 . . . and activated carbons 5 . . . are prepared by pulverizing raw material charcoal blocks into small pieces, granules, powder or fine powder and then sharp edges of these pieces or granules are rounded off by rubbing them against each other. Also, these charcoal pieces or granules are prepared in various sizes that some of them can permeate through the meshes (gaps) of the texture of the non-woven fabric sheets 1A, 1A while others cannot. And, those granules of pieces of Bincho charcoals 4... and activated carbons 5 ... capable of permeating through the texture constitute the fine powder carbides 4 . . . , 5 . . .

On the other hand, the water-absorbent polymers 2 . . . stored in the sealed enclosure 1 are of such sizes that they will not pass or escape through the meshes of the non-woven fabric sheets.

Also, since the respective polymers can be expanded by some hundreds of times with water absorption, the inside of the sealed enclosure 1, if it contains a large amount of water-absorbent polymers 2 . . . too will be expanded excessively, whereby the fluidity and cushioning effects of the polymers relative to each other will deteriorate to impair the handiness of the pouch. Considering this, the sealed enclosure 1 stores an appropriate amount of water-absorptive polymers 2 . . .

Figure 6:
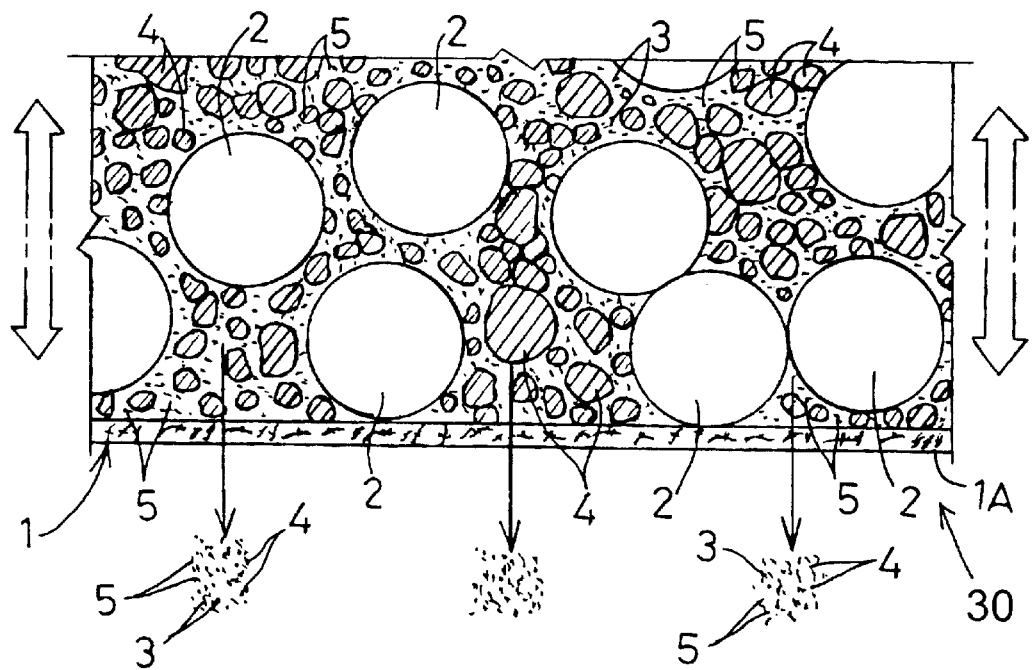
FIG. 6 is a section view showing the principal portions, in an enlarged scale, of the skin-care pouch under the condition shown in FIG. 2.
Figure 7:
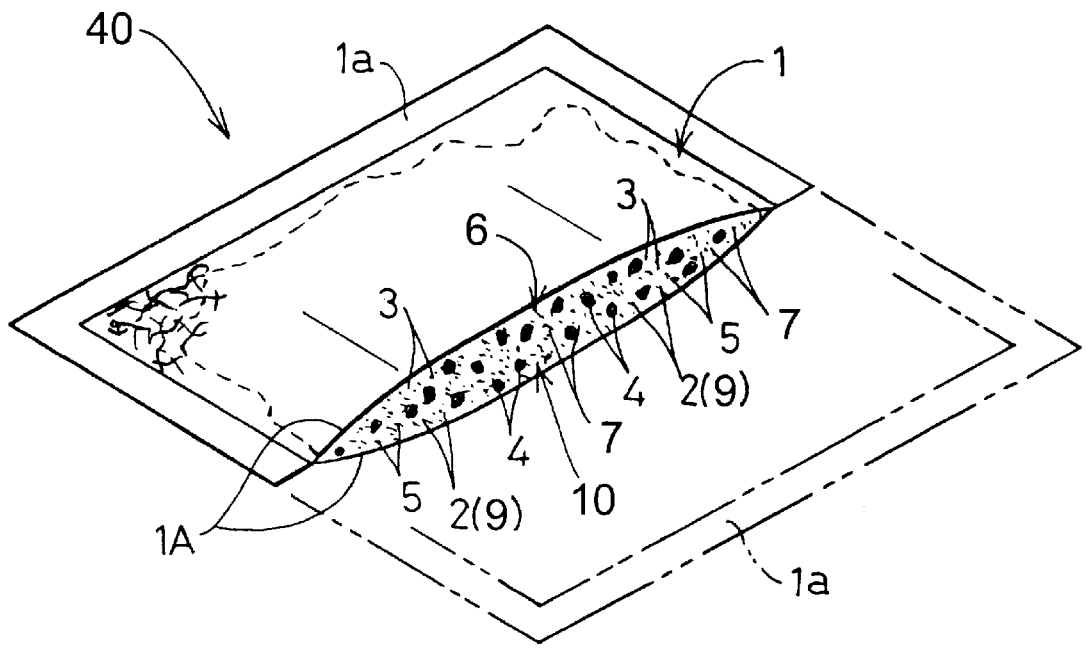
FIG. 7 is a perspective view showing a skin-care pouch according to a second embodiment of the invention in a condition when no water is supplied yet thereto.
Figure 8:
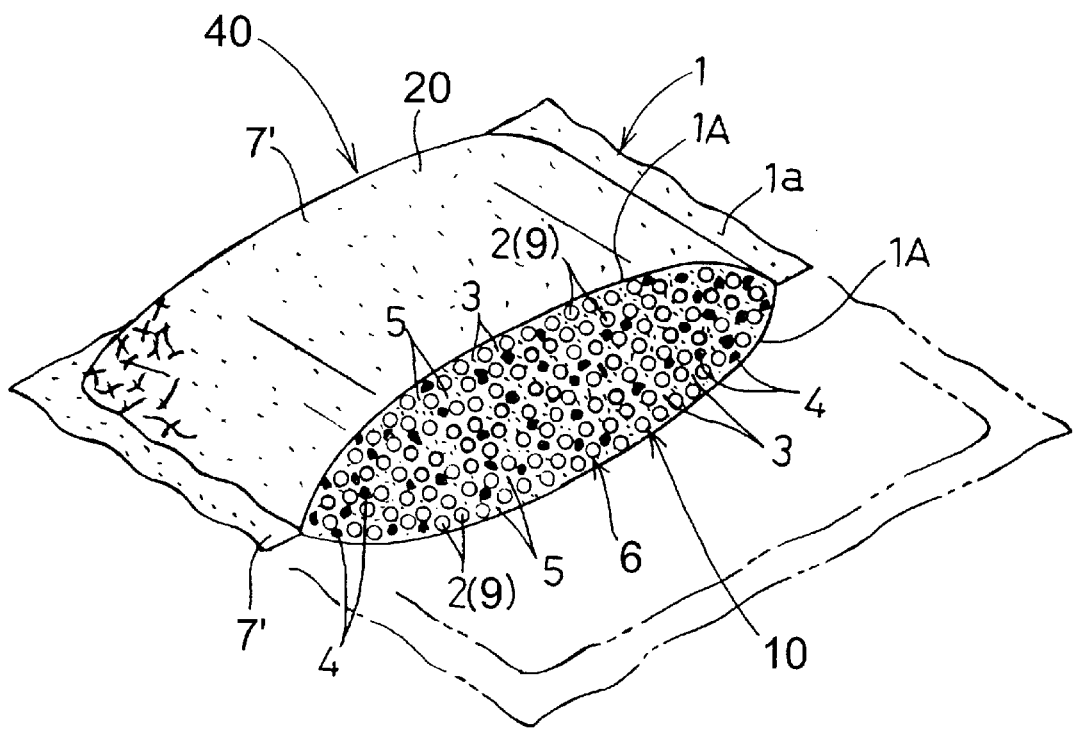
FIG. 8 is a perspective view showing the skin-care pouch according to the second embodiment in a condition when water has been supplied thereto.
Figure 9:
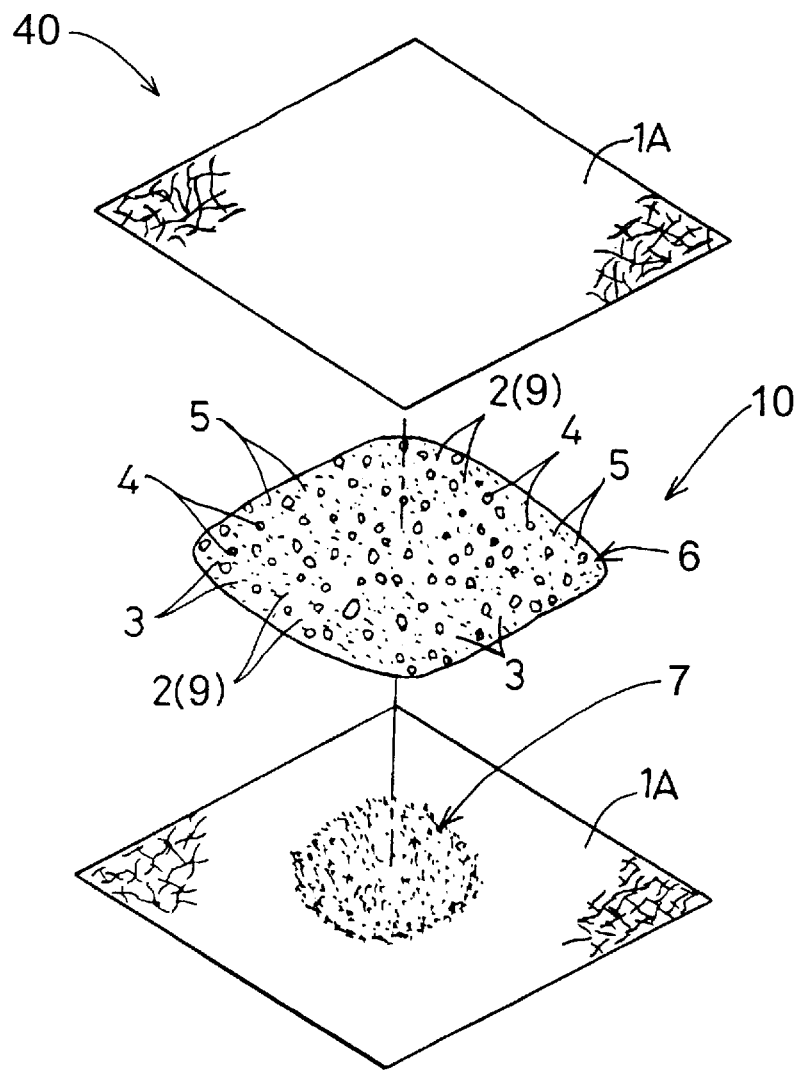
FIG. 9 is an exploded perspective view of the skin-care pouch according to the second embodiment.
Figure 10:
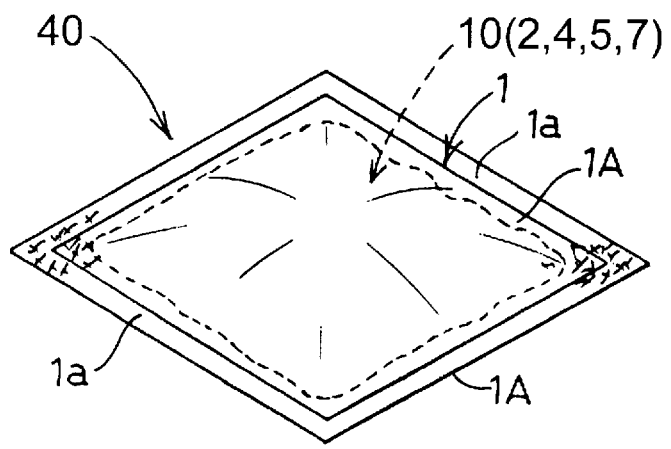
FIG. 10 is a perspective view showing the skin-care pouch according to the second embodiment in its finished condition as a commercial product.
Figure 11:
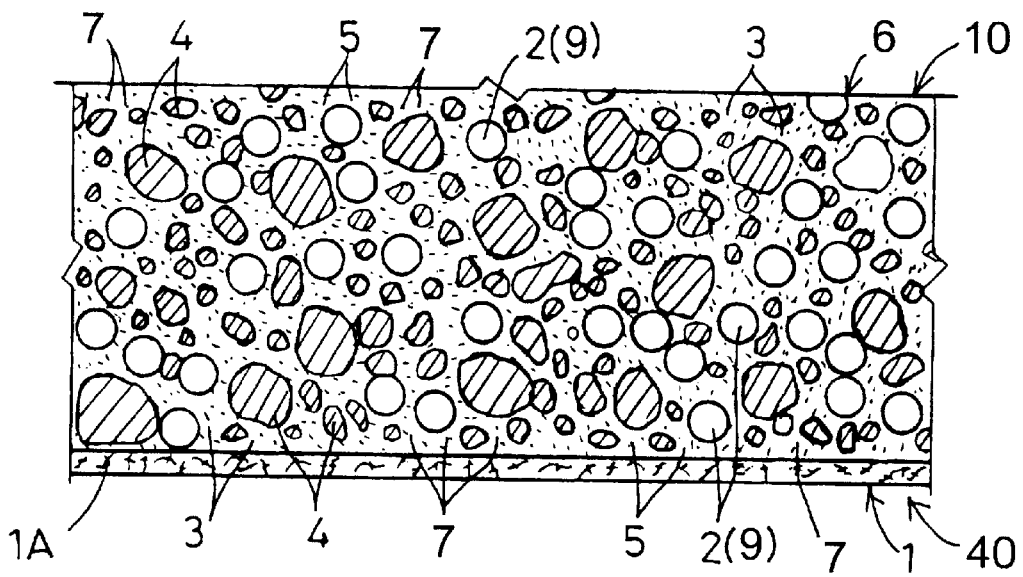
FIG. 11 is a section view showing principal portions, in an enlarged scale, of the skin-care pouch under the condition shown in FIG. 7.
Figure 12:
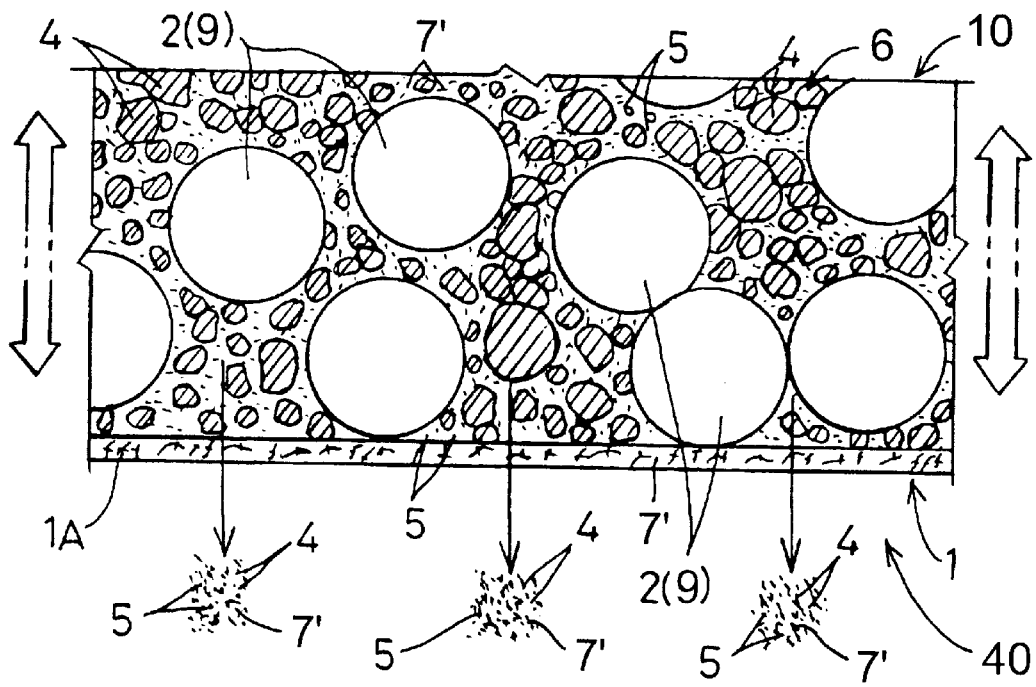
FIG. 12 is a section view showing the principal portions, in an enlarged scale, of the skin-care pouch under the condition shown in FIG. 8.

Further, since the polymers expanded by water absorption are not very adhesive to each other, the fluidity of the mixture content 10 inside the sealed enclosure 1 can be maintained. Therefor, by rubbing or squeezing the enclosure 1, as illustrated in FIG. 6, the carbides 4 . . . , 5 . . . present between the polymers containing water are rubbed against each other, so as to produce the carbides 4 . . . ,5 . . . in the form of fine powder which is small enough to pass the meshes or holes of the texture of the non-woven fabric sheets 1A, 1B. In the course of the above, since the Bincho carbides 4 are harder than the activated carbons 5, it is possible to produce the fine powder carbides 4 . . . , 5 . . . in an efficient manner by rubbing them each other.

As to the number of tourmaline ores 3 in the form of granules, tourmaline ore has a greater specific gravity than the others such as the Bincho charcoals 4, activated carbons 5, and the water-absorbent polymers 2, so that these granules of ore can easily escape through the meshes of the non-woven fabric sheets 1A. Therefore, the tourmaline ore granules 3 . . . stored within the enclosure 1 are mainly of granule sizes which are slightly larger than the meshes of the non-woven fabric 1A. Therefore, during application to the skin, an appropriate amount of tourmaline ores 3 . . . will be extruded through the meshes of the enclosure 1, so that the oozing amount of the tourmaline ores 3 . . . may be maintained to be equal to the initial amount after repeated uses of the pouch.

Next, there will be described a case in which the skin-care pouch 30 having the above-described construction is used for bathing.

First, the skin-care pouch 30 is soaked into warm water in a bathtub and then the enclosure 1 is rubbed so as to supply a sufficient amount of water to the water-absorbent polymers 2 . . . stored within the sealed enclosure 1.

After a while, the water-absorbent polymers 2 . . . will expand to swell up the sealed enclosure. Then, the pouch is removed out of the bathtub and put against a portion of the skin where treatment is desired by e.g. patting the pouch against the skin portion, whereby the number of Bincho charcoals 4 . . . , activated carbons 5 . . . in the form of fine powder and a number of tourmaline ores granules 3 . . . will ooze out to be applied to the skin portion.

Moreover, this skin-care pouch 30 permits repeated use by allowing the fine powder of Bincho charcoals 4 . . . , to ooze out gradually.

Then, after application to the required portion, the applied skin will be rinsed by warm or cold water.

After use, the skin-care pouch 30 can be just left to be ready for next or repeated use since proliferation of various germs or the like inside the pouch can be restricted by the antibacterial properties of the Bincho charcoals 4 and/or the activated charcoals 5 stored within the enclosure 1.

In the first embodiment described above, the carbide aggregations 6 consist of the Bincho charcoals 4 and the activated carbons 5. The invention is not limited to this construction. Instead, the carbide aggregations 6 may consist of either the Bincho charcoals 4 or the activated carbons 5 alone.

Further alternatively, the carbide aggregations 6 may comprise combination of the Bincho charcoals 4 and bamboo charcoals or a further combination of the Bincho charcoals 4, bamboo charcoals and the activated carbons 5.

In the first embodiment described above, the sealed enclosure 1 stores therein the mixture content 10 including a number of carbide aggregations 6 in the form of small pieces or granules, a number of water-absorbent polymers 2 . . . in the form of granules or powder acting as a water-absorbent shape-keeping agent which is gelled by absorbing water, and a number of tourmaline ores 3 . . . in the form of granules. The invention is not limited to this construction. Instead, the mixture content 10 to be stored within the sealed enclosure may comprise combination of a number of carbide aggregations 6 in the form of small pieces or granules and a number of water-absorbent polymers 2 . . . in the form of granules or powder acting as a water-absorbent shape-keeping agent which is gelled by absorbing water.

In the first embodiment described above, the water-absorbent shape-keeping agent comprise the number of water-absorbent polymers 2 . . . in the form of granules or powder. The invention is not limited to this construction. The water-absorbent shape-keeping agent may comprise a standard gelling agent such as gelatinizer.

[Second Embodiment]

As a second embodiment of the invention, a skin-care pouch 40 using wood vinegar will be described with reference to FIGS. 7 through 12.

This skin-care pouch 40 includes a sealed enclosure 1 which stores therein a mixed content 10 including wood vinegar 7 made into the form of powder, a number of carbide aggregations 6 in the form of small pieces or granules, a number of water-absorbent polymers 2 . . . in the form of granules or powder acting as a water-absorbent shape-keeping agent which is gelled by absorbing water, and a number of tourmaline ores 3 . . . in the form of granules.

For manufacturing the wood vinegar 7 in the form of powder, in this embodiment, first, some generated from a charcoal kiln during production of the Bincho charcoal (a kind of hard charcoal) is cooled and liquefied to obtain a liquid concentrate, which is then diluted or refined to obtain the wood vinegar liquid. Thereafter, this wood vinegar liquid is subjected to e.g high-speed freeze-drying method to be sublimated and dehydrated, whereby the powder wood vinegar 7 . . . is obtained.

The resultant wood vinegar powder 7 . . . retains substantially all of the components of wood vinegar and can be made back into wood vinegar liquid 7'.

Also, it is possible to increase the concentration of the wood vinegar liquid 7' eluted for use by storing a large amount of wood vinegar powder 7 in the sealed enclosure 1. Conversely, the concentration can be reduced by storing a small amount of wood vinegar powder 7 therein.

The sealed enclosure 1 is of a texture having meshes allowing permeation of water 20 (sometimes, warm water is employed), the liquefied wood vinegar 7', the powder carbides 4 . . . , 5 . . . and this enclosure is non-woven fabric sheets 1A, 1A formed mainly of synthetic resin. The methods of forming this sealed enclosure 1 are same as those described in the first embodiment and therefore will not be described in repetition here.

Further, the constructions of the carbide aggregates 6, the water-absorptive polymers 3 . . . constituting the water-absorptive cushioning material 9 of the sealed enclosure 1, and of the number of tourmaline ore granules 3 . . . are same as those described in the first embodiment and therefore will not be described in repetition here.

Next, an exemplary use of the wood-vinegar pouch 40 having the above construction for bathing will be described.

First, the skin-care pouch 40 is soaked in warm water in the bathtub and the sealed enclosure 1 is squeezed and rubbed therein to supply a sufficient amount of water to the water-absorbent polymers 2 . . . inside the enclosure.

After a while, the wood vinegar powder 7 . . . will elute and at the same time the water-absorbent polymers 2 . . . will expand to swell out the sealed enclosure 1. Then, the pouch is removed out of the tub and patted against a desired skin portion needing care, such as the face skin, whereby the liquefied wood vinegar 7', the fine powders of the Bincho charcoals 4 . . . activated carbons 5 . . . , and the tourmaline ore granules 3 . . . will ooze out of the enclosure 1 to be applied to the face skin.

Then, after completion of application to the desired portion, the applied skin portion will be rinsed with warm or cold water.

With this skin-care pouch 40, with the initial supply of water thereto, the wood vinegar powder 7 . . . is liquefied, so that after repeated soaking of the pouch in warm or cold water, the concentrations of the wood vinegar 7' permeated through the pouch and the wood vinegar liquid 7' inside the enclosure are gradually reduced.

[Third Embodiment]

Figure 13:
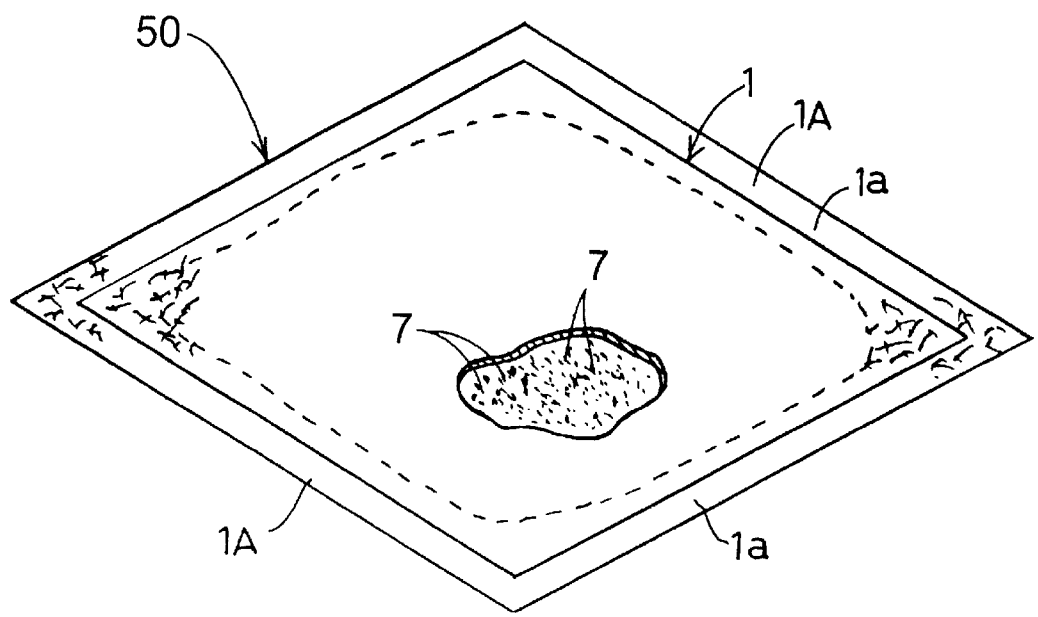
FIG. 13 is a perspective view showing a skin-care pouch according to a third embodiment of the invention in a condition when no water is supplied yet thereto.
Figure 14:
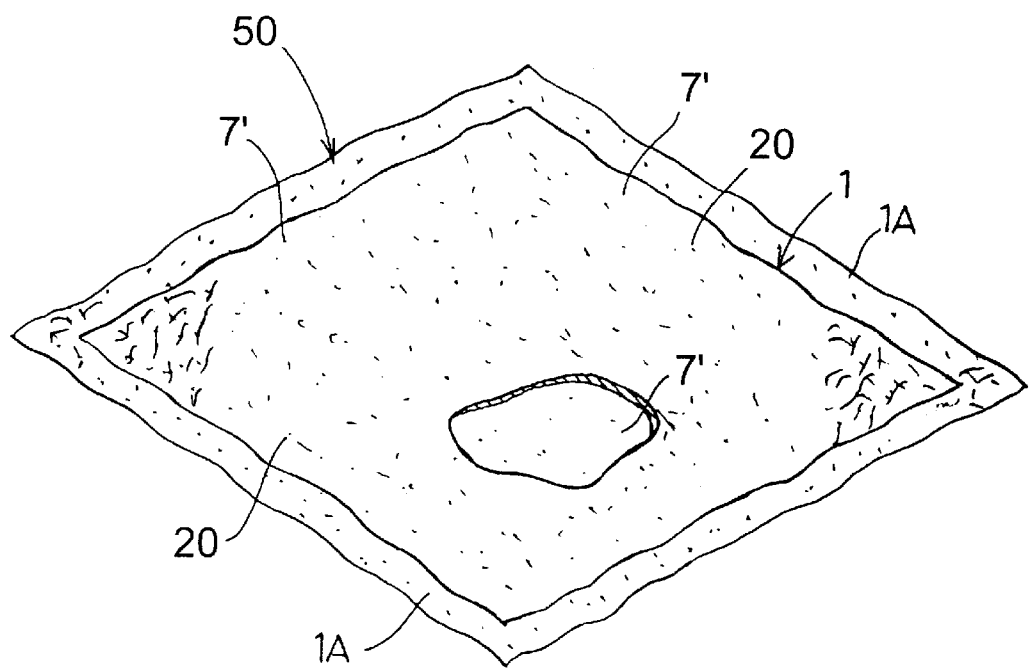
FIG. 14 is a perspective view showing the skin-care pouch according to the third embodiment in a condition when water has been supplied thereto.

As shown in FIGS. 13 and 14, a wood-vinegar skin-care pouch 50 according to this third embodiment includes a sealed enclosure 1 storing therein wood vinegar 7 . . . in the form of powder.

The sealed enclosure 1 is formed of non-woven fabric sheets 1A, 1A made mainly of synthetic resin having a texture with meshes capable of permeating water 20, the liquefied wood vinegar 7' therethrough.

With this construction, by supplying water to the skin-care pouch 50, the wood vinegar powder 7 . . . in the enclosure 1 will be dissolved and soak into the sealed enclosure 1 and the liquefied wood vinegar 7' will ooze out of the sealed enclosure 1.

[Fourth Embodiment]

Figure 15:
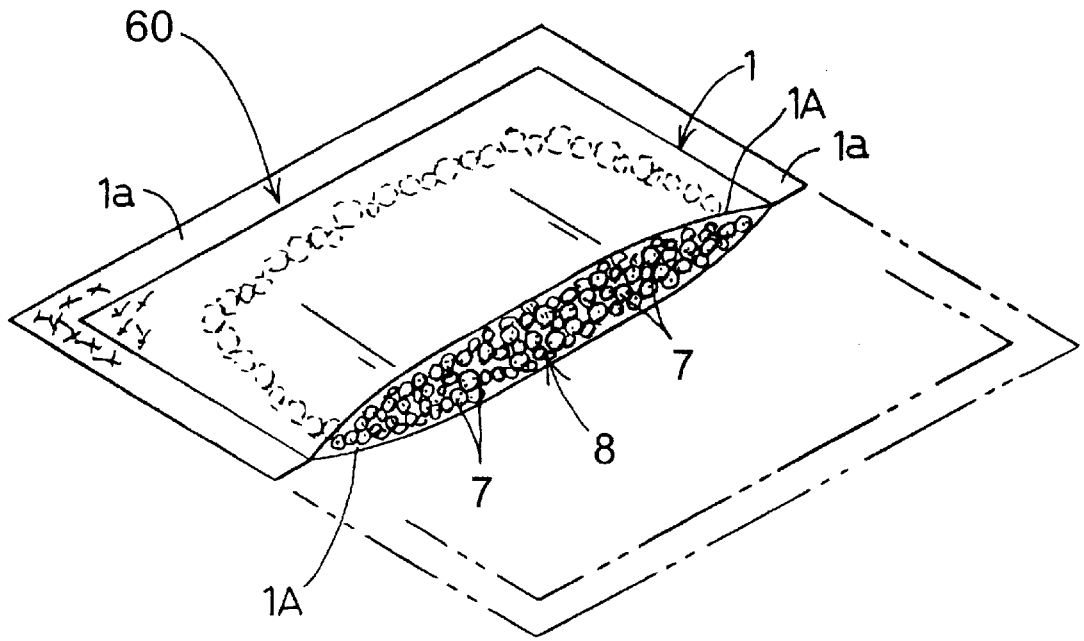
FIG. 15 is a perspective view showing a skin-care pouch according to a fourth embodiment of the invention in a condition when no water is supplied yet thereto.
Figure 16:
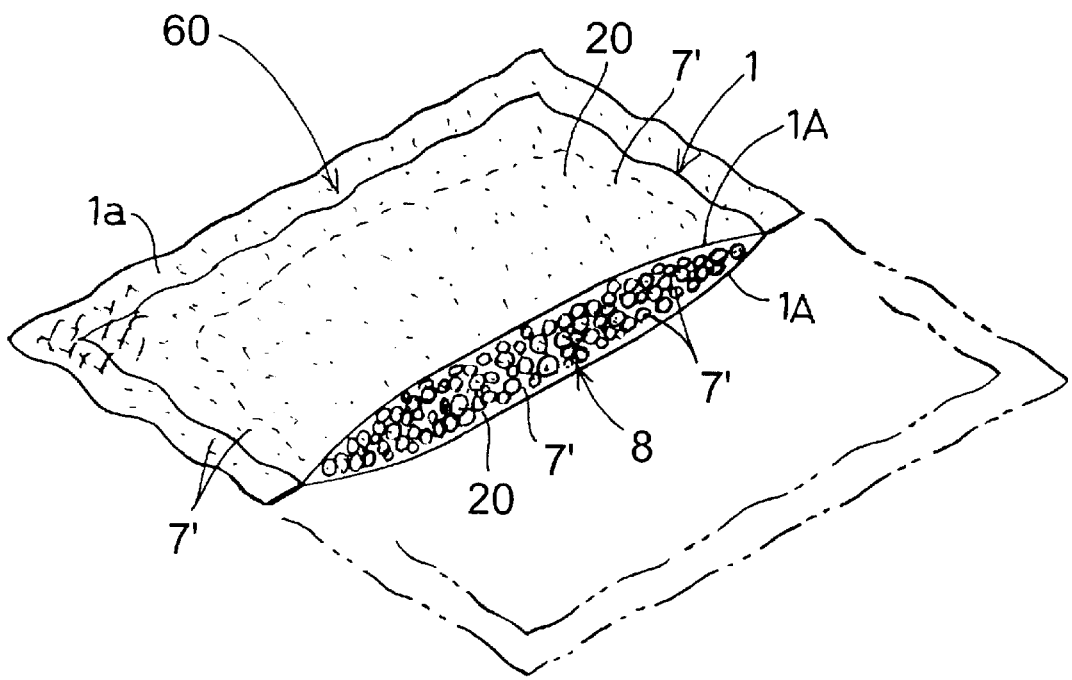
FIG. 16 is a perspective view showing the skin-care pouch according to the fourth embodiment in a condition when water has been supplied thereto.

As shown in FIGS. 15 and 16, a wood-vinegar skin-care pouch 60 according to this fourth embodiment includes a sealed enclosure 1 storing therein a number of gel aggregates 8 in the form of small pieces or granules impregnated with liquefied wood vinegar 7', the enclosure being made of a fabric capable of permeating water therethrough.

The gel material forming the gel aggregations may comprise gelatinizer.

In the case of this fourth embodiment, the gel aggregations 8 are prepared by impregnating the liquefied wood vinegar 7' therein in the course of gelatinization and provided in the form of small pieces or granules.

With this construction, as the gel aggregations 8 giving soft feel are accommodated within the sealed enclosure 1, the sealed enclosure 1 with the wood vinegar 7' liquefied with supply of water can give soft feel to the skin during application.

{Fifth Embodiment]

Figure 17:
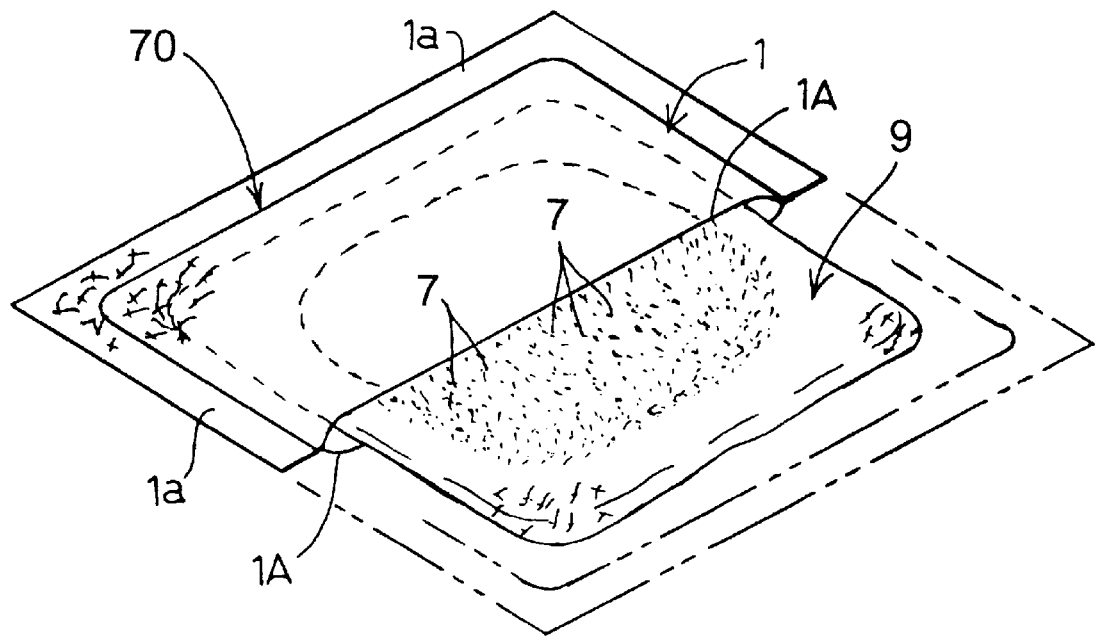
FIG. 17 is a perspective view showing a skin-care pouch according to a fifth embodiment of the invention in a condition when no water is supplied yet thereto.
Figure 18:
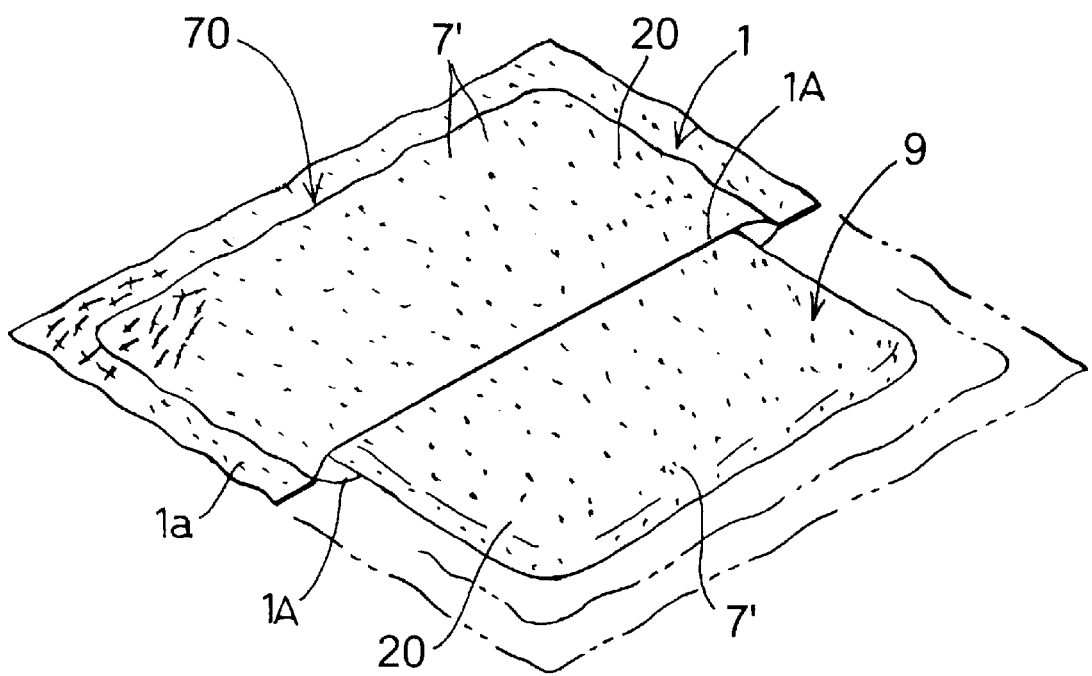
FIG. 18 is a perspective view showing the skin-care pouch according to the fifth embodiment in a condition when water has been supplied thereto.

As shown in FIGS. 17 and 18, a wood-vinegar skin-care pouch 70 according to this fifth embodiment includes a sealed enclosure 7 storing therein wood vinegar powder 7 . . . and a water-absorbent cushioning material 9, the enclosure being formed of a fabric capable of permeating water and liquefied wood vinegar 7' therethrough.

The water-absorbent cushioning material 9 may comprise at least one of cotton or sponge which has a cushioning property under a normal condition, a gelling agent as water-absorbent shape-keeping agent such as gelatinizer or a number of water-absorbent polymers as water-absorbent shape-keeping agent in the form of granules or powder. In case the water-absorbent cushioning material 9 is formed of cotton or sponge, this may be stored within the sealed enclosure as a single large lump or a number of small lumps.

With this construction, the liquefied wood vinegar 7' oozing out of the sealed enclosure 1 may be applied to the skin while the sealed enclosure 7 provides soft and comfortable feel to the skin.

[Other Embodiments]

In the respective embodiments described above, the mixture content 10 stored within the sealed enclosure may further include a number of cypress chips soaked with cypress oil as an aromatic component.

Further, in the respective embodiments described above, the mixture content 10 may still further include a natural medication containing a moisture-keeping component for the skin.

In this case, with supply of water to the sealed enclosure, the natural medication will elute in the water and ooze out of the enclosure to be applied to the skin.

Specific examples of such natural medication include one of chamomile (manzanilla), leaf of grape, seaweed, etc. of two more thereof in combination.

In the respective embodiments described above, the sealed enclosure 1 is formed by heating fusing together the non-woven fabric sheets 1A, 1A made mainly of synthetic resin. The invention is not limited to this construction. Alternatively, the sealed enclosure may be formed by using an adhesive agent, regardless of the composition of the non-woven fabric.

Further, instead of non-woven fabric, the sealed enclosure 1 may be formed of thin cotton fabric sheet, thick cotton fabric sheet, laminated fabric with non-woven fabric laminated with a cotton sheet, small-mesh gauze fabric, or cotton pile fabric. etc. If a thick fabric is used for the sealed enclosure 1, the skin-care pouch 70 can provide soft and comfortable skin feel.

Having described the presently preferred embodiments of the invention, it is to be understood that they may be embodied otherwise within the scope of the appended claims.

What is claimed is:

1. A skin-care pouch comprising:
    a number of carbide aggregations including carbides in the form of small pieces, granules or particles;
    water-absorbent shape-keeping agent which is gelled by absorbing water upon contact therewith; and
    a sealed enclosure storing the carbide aggregations and the water-absorbent shape-keeping agent therein, the sealed enclosure being formed of a fabric capable of permeating water and the carbides therethrough.

2. The skin-care pouch according to claim 1, wherein the carbide aggregations comprise hard charcoal.

3. The skin-care pouch according to claim 1, wherein the carbide aggregations comprise bamboo charcoal.

4. The skin-care pouch according to claim 1, wherein the carbide aggregations further include activated carbon.

5. The skin-care pouch according to claim 1, wherein the water-absorbent shape-keeping agent comprises a number of water-absorbent polymers in the form of granules or powder.

6. The skin-care pouch according to claim 1, wherein the water-absorbent shape-keeping agent comprises gelling agent.

7. The skin-care pouch according to claim 1, wherein the sealed enclosure is formed of non-woven fabric made mainly of a synthetic resin which can be sealed by heat.

8. The skin-care pouch according to claim 1, wherein the sealed enclosure further stores therein chips impregnated with aromatic substance.

9. The skin-care pouch according to claim 1, wherein the sealed enclosure further stores therein tourmaline ores in the form of granules.

10. The skin-care pouch according to claim 1, wherein the sealed enclosure further stores therein natural medication containing skin moisture keeping component.

* * * * *